United States Patent [19]

Moore

[11] Plant 4,368

[45] Jan. 16, 1979

[54] ROSE PLANT

[76] Inventor: Ralph S. Moore, 2519 E. Noble Ave., Visalia, Calif. 93277

[21] Appl. No.: 830,355

[22] Filed: Sep. 2, 1977

[51] Int. Cl.[2] ..... A01H 5/00

[52] U.S. Cl. ..... Plt./10

[58] Field of Search ..... Plt./7, 10

*Primary Examiner*—Robert E. Bagwill
*Assistant Examiner*—James R. Feyrer

[57] ABSTRACT

The subject of this invention is a new and distinct variety of miniature rose characterized primarily by its deep red many petaled flowers and its much branched compact plant with medium green, disease resistant, foliage.

1 Drawing Figure

1

The present invention relates to a new and distinct variety of hardy, dwarf, bush type rose plant of the miniature class; the buds and flowers which in general color effect are similar to Little Curt (miniature — not patented).

The variety is further characterized by:

An abundance of bloom, with flowers borne singly or several to the stem in loose clusters.

Little or no fragrance.

A plant which is vigorous, of rounded upright shape with semi-glossy small foliage with pointed leaflets; the buds and flowers being similar in form and size to Starina (minature — U.S. Plant Pat. No. 2,446).

The plant, which has a normal height of 12–14 inches, can easily be maintained at lesser height by occasional trimming.

A plant which grows and blooms satisfactorily both in greenhouse and outdoors; is good for growing in pots, and provides excellent garden decoration as well as cut flowers.

The present variety of miniature rose was originated by me at Sequoia Nursery, located at Visalia, Calif., under conditions of careful control and observation, as a cross between Red Pinocchio (U.S. Plant Pat. No. 812, expired) Floribunda, as the seed parent and Little Chief (miniature — not patented), as the pollen parent.

Subsequent to origination of the variety I successfully asexually reproduced it, at Sequoia Nursery, located as aforesaid, by budding as well as by cuttings, the reproductions having run true in all respects.

The color photograph illustrates the variety, including the foliage, buds and flowers.

Referring now specifically to the new and distinct variety of minature rose plant, the following is a detailed description thereof in outline; all major color plate identifications being by reference to the British Colour Council Horticultural Colour Chart, except where common terms of color definition are employed.

Type: Hardy; dwarf; bushy; rounded to upright; seedling; greenhouse; outdoors; cut flowers; garden decoration; potted plant.

Class: Miniature. Variety name: FIESTA RUBY.

Flowers borne: Singly and several together (3–5) on slender wirey stems.

Quantity of bloom: Abundant both outside and in greenhouse.

Bud: Peduncle — medium to short length (15–20 mm — sometimes longer); slender, erect; medium green, sometimes tinted bronze (outdoors); hairs — several — very short. Before calyx breaks; size — small.

2

Form — short (ovoid); pointed with several foliaceous appendages and few or no hairs on surface of bud; with foliaceous parts extending beyond the tip of the bud equal to one-half or less of its length. Color — medium green, occasionally tinted with bronze (outdoors). As calyx breaks: color — deep red — near Cardinal red 822/3. Opening: opens well in all weather.

Bloom: Size when fully open — small, averaging about 30–35 mm. Petalage — double, averaging about 40 petals, arranged regularly plus sometimes several small petaloids. Form — high center at first, remaining rather high, with petals rolled loosely outward, and later at maturity open with petals folded at edge to give a pointed effect and rolled loosely outward and downward. Open flowers usually show stamens.

Petals: Fairly thick; satiny on inside and on outside surfaces. Shape — outside petals: broad lanceolate (nearly oval) with rounded tip; intermediate — broad lanceolate with rounded tip; inside — lanceolate with rounded tip.

Color: Newly opened flower from a plant grown outdoors (Aug. 1977), Visalia, Calif.:

*Outside petal.*—Outside surface — near Cardinal Red 822/2 overlaid on upper one-half with darker red — near Chrysanthemum Crimson 824/1 (may also be lighter red shade) and becoming white or yellowish toward base. Inside surface — near Chrysanthemum Crimson 824 (may be lighter red near tip) with small yellow area at base.

*Intermediate petal.*—Outside surface — similar to outside petal. Inside surface — similar to outside petal.

*Inner petal.*—Outside surface — same as intermediate petal. Inside surface — same as intermediate petal.

General color effect; newly opened flowers — deep red. Three days open — color similar to newly opened flowers but ligher color. Behavior — opens well in all weather. Spent petals drop off. Flower longevity (July - August 1977) plant in pot 4–6 days or longer. Cut flowers at living room temperature 4 days or longer.

Reproductive organs:

*Stamens.*—Abundant, arranged regularly about pistils.

*Filaments.*—Varying length, fairly short; yellow.

*Anthers.*—Well formed, yellow.
*Pollen.*—Moderate amount.
*Pistils.*—Average number.
*Styles.*—Fairly even; short; bunched.
*Stigmas.*—Whitish.
*Ovaries.*—All enclosed in calyx.
*Hips.*—Few or none.
*Sepals.*—Permanent; spear shaped, recurved.
*Seed.*—Few or none.

Foliage:

*Leaves.*—Compound of five (sometimes three or seven) leaflets; medium to small; leathery; semi-glossy.

*Leaflets.*—Shape: broad lanceolate, nearly oval; apex acute; base rounded or rounded acute. Margin serrate. Color: medium green; new growth — normal (medium) green — sometimes reddish (outdoors). Rachis: medium strength; upper side may have a few tiny short hairs, grooved; underside sparsely thorny with few or no tiny prickles. Stipules: medium long; narrow to medium width; medium length narrow points which turn out usually at about 45 degrees or more.

Growth:

*Habit.*—Dwarf; bushy; rounded; upright; much branched.

*Growth.*—Free; vigorous; internodes short.

*Canes.*—Medium; slender, sturdy.
*Main stems.*—Color: medium green.
*Thorns.*—Average; slender; hooked slightly downward; color — brown. Prickles — none. Hairs — none.
*Branches.*—Color: medium green. Thorns: average; short length; slender; hooked. Medium to short oval base. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy; dwarf, bushy, much branched habit, substantially as illustrated and described, characterized by buds and flowers which are deep red, the color resembling Little Curt (miniature — not patented) and the miniature rose, Starina (U.S. Plant Pat. No. 2,646) in general form and size; and further characterized by a plant which is vigorous and compact with abundant medium to small size, semi-glossy, disease resistant foliage, easy to propagate from cuttings and by budding, with an abundance of flowers borne singly or several to the stem in moderately loose clusters.

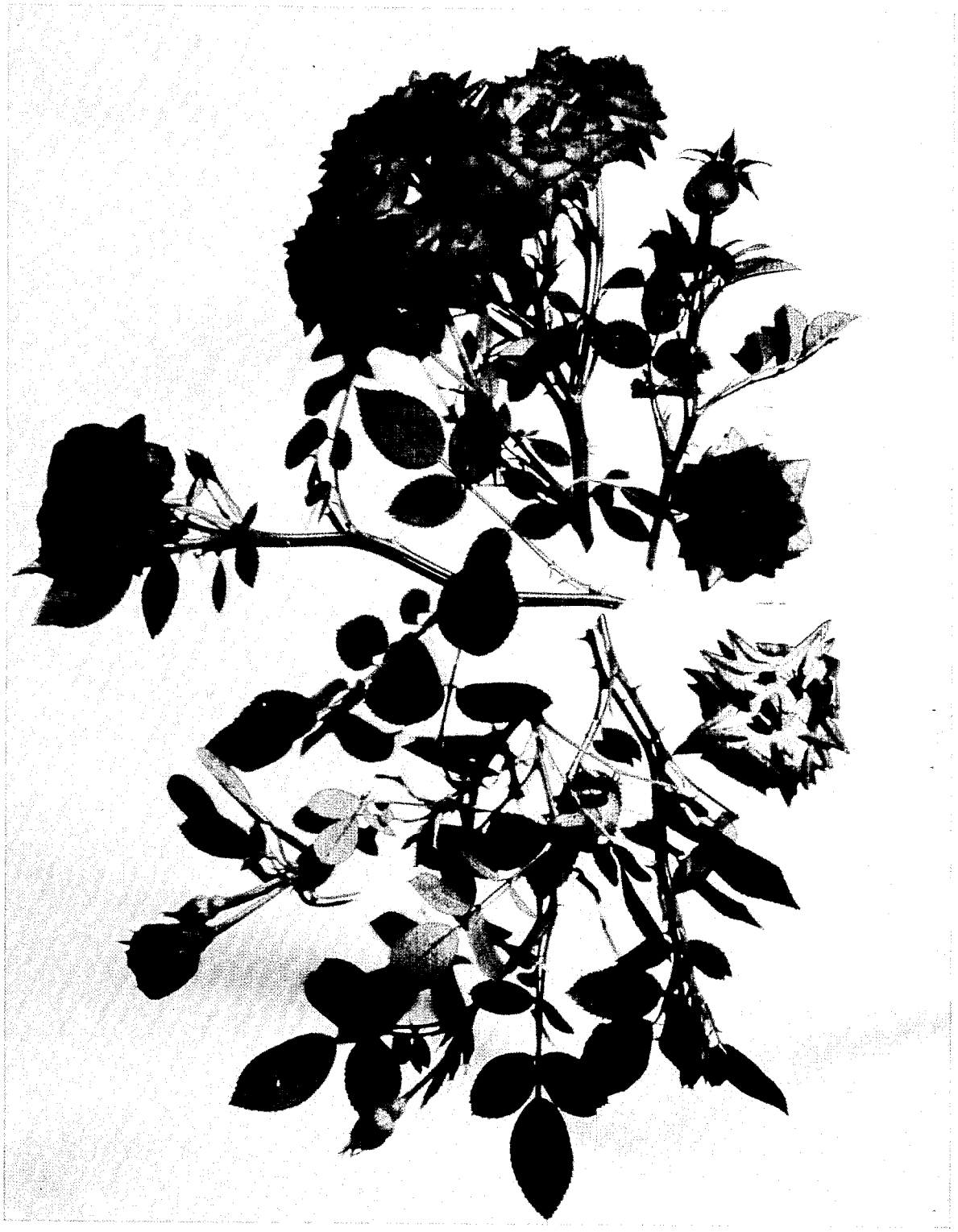

* * * * *